United States Patent
Schumacher et al.

(10) Patent No.: US 7,917,018 B2
(45) Date of Patent: Mar. 29, 2011

(54) WEARABLE CHEMICAL DISPENSER

(75) Inventors: Donald J. Schumacher, Racine, WI (US); Raymund J. Alfaro, Oak Creek, WI (US); Dirk K. Nickel, Mukwonago, WI (US); Tyler D. Duston, Evanston, IL (US); Michael T. Hudak, Racine, WI (US); Sean P. Kingston, Oak Creek, WI (US); Anne T. Maghasi, Racine, WI (US); Kwamena Gyakye deGraft-Johnson, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 12/822,791

(22) Filed: Jun. 24, 2010

(65) Prior Publication Data
US 2010/0270393 A1 Oct. 28, 2010

Related U.S. Application Data

(62) Division of application No. 11/773,097, filed on Jul. 3, 2007, now Pat. No. 7,833,492.

(51) Int. Cl.
| | |
|---|---|
| A61L 9/00 | (2006.01) |
| A62B 7/08 | (2006.01) |
| A24F 25/00 | (2006.01) |
| A61M 16/00 | (2006.01) |
| F26B 19/00 | (2006.01) |
| F26B 17/00 | (2006.01) |
| A01M 13/00 | (2006.01) |

(52) U.S. Cl. .............. 392/390; 422/1; 422/5; 422/123; 422/124; 422/125; 239/35; 239/55; 239/56; 34/579; 34/587; 34/87; 34/192; 43/1; 43/125

(58) Field of Classification Search ............. 239/35, 239/55–56; 392/390; 422/1, 5, 123–125; 34/579, 587, 87, 192; 43/1, 125
See application file for complete search history.

(56) References Cited

U.S. PATENT DOCUMENTS

| | | | |
|---|---|---|---|
| D246,319 S * | 11/1977 | Rabussier et al. | ............ D23/369 |
| 4,062,649 A | 12/1977 | Kuderna et al. | |
| 4,293,095 A | 10/1981 | Hamilton et al. | |
| 4,824,827 A | 4/1989 | Kelly et al. | |
| 4,921,636 A * | 5/1990 | Traas | ................. 252/408.1 |

(Continued)

FOREIGN PATENT DOCUMENTS

EP     227167     7/1987

(Continued)

OTHER PUBLICATIONS

PCT/US2008/008289 International Search Report and Written Opinion dated Jan. 14, 2009.

*Primary Examiner* — Jill Warden
*Assistant Examiner* — Monzer R Chorbaji (57) ABSTRACT

Disclosed herein are wearable devices for dispensing insect repellents, fragrances, and/or other chemicals along the outside of the clothing of a human, to avoid the need to apply such chemicals directly to clothing or to human's skin. The devices have an on/off switch that automatically controls a shutter which enables and restricts air flow, while also controlling fan operation and covering of a use-up cue. The device also is designed to prevent fan operation when an impregnated slab is not present. Also disclosed are preferred refills for use with such devices.

5 Claims, 11 Drawing Sheets

U.S. PATENT DOCUMENTS

| | | |
|---|---|---|
| 5,293,648 A | 3/1994 | Finley |
| 6,371,450 B1 | 4/2002 | Davis et al. |
| 6,582,714 B1 | 6/2003 | Emmrich et al. |
| 6,926,902 B2 | 8/2005 | Inoue et al. |
| 7,007,861 B2 | 3/2006 | Ketcha et al. |
| 7,152,809 B2 | 12/2006 | Ketcha et al. |
| 7,168,630 B1 | 1/2007 | Ketcha et al. |
| 7,175,815 B2 | 2/2007 | Yamasaki et al. |
| 2003/0044326 A1 | 3/2003 | Yamasaki |
| 2003/0175171 A1 | 9/2003 | Yamamoto et al. |
| 2004/0076553 A1* | 4/2004 | Zobele et al. .................. 422/123 |
| 2005/0079113 A1 | 4/2005 | Selander |
| 2006/0039835 A1 | 2/2006 | Nottingham et al. |
| 2006/0137241 A1 | 6/2006 | Yamasaki et al. |
| 2007/0036688 A1 | 2/2007 | Hayes-Pankhurst et al. |

FOREIGN PATENT DOCUMENTS

| | | |
|---|---|---|
| EP | 1698228 | 9/2006 |
| GB | 1475004 | 6/1977 |

* cited by examiner

WEARABLE CHEMICAL DISPENSER

CROSS-REFERENCE TO RELATED APPLICATIONS

This is a divisional application claiming priority based on U.S. patent application Ser. No. 11/773,097, which was filed on Jul. 3, 2007 now U.S. Pat. No. 7,833,492.

STATEMENT REGARDING FEDERALLY SPONSORED RESEARCH/DEVELOPMENT

Not applicable

BACKGROUND OF THE INVENTION

The present invention relates to wearable devices that dispense chemicals such as insect repellents and/or fragrances.

Various techniques have been developed to provide humans with protection from insect bites. For insect control inside buildings a primary emphasis is placed on trying to keep insects from entering the building at all (e.g. placing screens over windows). This sometimes is supplemented with chemical treatment of room air and/or the use of traps. See e.g. U.S. Pat. Nos. 6,582,714 and 7,175,815, and also U.S. patent application publications 2005/0079113, 2006/0039835, 2006/0137241 and 2007/0036688.

When the individual is outdoors where the area can't be effectively screened, and the individual is mostly staying in a particular area (e.g. at a picnic, or on a patio near a building), traps and repellents are the primary focus. For example, a common approach is to use candles (e.g. citronella candles) or other dispensing devices which disperse repellents such as citronella into the air.

Alternatively, and in any event when the individual is moving away from a single area that they control, individuals often apply an insect repellent to clothing or directly to their skin. The source of repellent protection thus moves with the individual.

However, if a consumer does not read the label or other instructions associated therewith they may not understand how long a particular application of the chemical is likely to remain most effective. This may lead the consumer to prematurely apply additional product before it is necessary to do so, thereby increasing the overall cost of protection. Alternatively, they may not make a repeat application of product soon enough, until after the effectiveness of the product has decreased dramatically. This may lead to consumer dissatisfaction.

In any event, some conventional insect repellent sprays/lotions sometimes raise concerns deriving from the location where the chemical is to be applied. For example, where the product is intended to be sprayed on clothing, this will limit how the spray is formulated (e.g. to avoid using certain otherwise preferred solvents or actives that can stain certain fabrics). This can increase costs, or require some compromises with respect to other desired attributes (e.g. perceived feel). Moreover, even where the formulations are designed to be sprayed directly on even very delicate clothing, consumers may be unwilling to test that out, and thus avoid the product regardless of its suitability.

Similarly, notwithstanding suitability, some consumers have expressed a reluctance to apply insect repellents directly to their skin. Again, this can lead to consumers avoiding products which direct that type of application.

As a result, the art has attempted to develop compact, portable electrical devices having a fan and an insecticide source therein. These devices may have a clip so that they can easily be mounted on a belt, a purse, or even a pocket, and thus be "worn" by the consumer as they move outside. The device may draw air through, or blow air past, a substrate impregnated with an insect repellent or other air treatment chemical, thereby dispensing the active into the air, preferably (in the case of a repellent) downward along the outside of a human's clothing. See e.g. U.S. Pat. Nos. 6,296,902, 7,007,861, 7,152,809, and 7,168,630, and U.S. patent application publication 2003/0175171.

There have even been a variety of attempts to develop use indicators associated with air treatment devices, so that consumers can tell when the device needs servicing/refilling. See e.g. U.S. Pat. Nos. 4,062,649, 4,293,095, 4,824,827, 5,293,648. See also U.S. Ser. No. 11/609,923, filed Dec. 13, 2006.

However, some such devices blow the active too far out away from the human body, causing too little of the active to reach locations of primary concern (e.g. near ankles). Other such devices don't provide a way of minimizing waste of the active, such as while blower operation is suspended between uses. Still other such devices are unduly costly, are too heavy, or have other deficiencies (such as not providing sufficient feedback to the consumer when the device is otherwise operating ineffectively).

Hence, a need exists for improved devices for dispensing insect control actives and other air treatment chemicals, particularly those that can operate without applying chemicals directly to the skin or clothing.

BRIEF SUMMARY OF THE INVENTION

The present invention provides a dispensing device for dispensing an air treatment chemical. The device has a housing with an inlet and an outlet and an electrically powered fan to pull air in through the inlet and exhaust the air through the outlet, creating an air stream through the housing. There is also a switch for turning the fan on and off, and a movable shutter.

Particularly importantly the shutter blocks the air flow when in a first, closed position and allows the air to flow when in a second, open position. It also has a projection thereon that interacts with the switch so that moving the shutter to the second, open position activates the switch to turn on the fan.

In preferred forms there is also a rotatable finger that must be rotated by interaction with the projection of the shutter before the switch can be activated. There is a table to receive and hold a substrate exposed to the air stream, where the substrate bears an air treatment chemical to be dispensed. The substrate is held in interactive relation with the finger so (as it is being installed) to partially rotate the finger from a designated position when no substrate is held by the table, to a selected position when a substrate is held by the table. When the finger is in the selected position it can be further rotated there from by movement of the projection as the shutter is moved to activate the fan.

In other preferred forms the substrate comprises a use-up cue that changes appearance by evaporation of a material in a direction toward the table when the substrate is in place on the table, wherein the finger has a side extension that, as the finger is rotated by interaction with the projection of the shutter as the shutter is moved, moves from a position inhibiting the evaporation of material from the use-up cue to a second position wherein evaporation of material from the use-up cue is readily permitted. The shutter, when in its closed position, can close both the inlet and outlet.

In another aspect the invention provides a refill substrate for use with such a device. For example, the substrate can have an air-permeable structure containing the air treatment chemical to be dispensed, and a surface positioned to interact with the finger so as to rotate it to the selected position. It may also have a use-up cue such that, when the substrate is in place on the table of the dispensing device, the use-up cue changes appearance by evaporation of a material in a direction toward the table and at a location such that a side extension of the finger, when the shutter is in its closed position, blocks evaporation of material from the use-up cue.

In still another aspect of the invention there is provided a wearable device for dispensing an air treatment chemical. It has a housing having an inlet for permitting air to enter into an internal cavity of the housing and an outlet for permitting air mixed with air treatment chemical to exit the cavity. There is also a power supply mounted to the housing, a substrate positionable in the housing bearing an air treatment chemical, a blower powered by the power supply and capable of moving air from the inlet adjacent the substrate so as to mix air treatment chemical into the moving air, and then deliver a mix of air and air treatment chemical to outside of the housing, and a shutter that can control air flow through the device.

Preferably the shutter can restrict air flow through the inlet at a same time the shutter restricts air flow through the outlet, when the blower of the device is not operating. Further, the shutter can have linked thereto a cam projection which, when the substrate is in the device and the projection is moved to a selected position, can cause an activation of the blower. If the substrate is removed from the device movement of the cam projection to the selected position doesn't activate the blower.

Other preferred aspects include that the substrate has an air permeable section bearing the air treatment chemical and a shell portion containing a volatile use-up cue chemical. There is a finger mounted for rotation on its own longitudinal axis. A portion of the finger can permit diffusion of the use-up cue chemical from the shell when the finger is in a first rotational position, and can restrict diffusion of the use-up cue chemical from the shell when in a second rotational position. Movement of a cam projection can drive the finger from the second rotational position to the first rotational position.

The finger preferably automatically moves to a third rotational position when the substrate is not present, and when so positioned placing the substrate in the device can drive the finger to the second rotational position. When the finger is in the second rotational position a cam projection on the shutter can extend through a through slot on the substrate to drive the finger to the first rotational position, and when the finger thereby reaches the first rotational position the blower will be activated.

In a further aspect the invention provides a refill substrate for use with a wearable air treatment chemical dispenser. There is a slab structure having opposed facing surfaces, a through hole extending between the facing surfaces, an air permeable sheet extending across the through hole, the sheet bearing a volatile insect repellent, and a support beam extending at least part way across the through hole to support the sheet.

In preferred forms the slab structure also has a shell cavity retaining a use-up cue chemical, the cavity having an essentially transparent wall along one of the opposed facing surfaces, the shell cavity is covered by a peel-off cover along the other of the opposed facing surfaces, there is a through slot positioned between the air permeable section and the shell, and there is an indentation along a peripheral portion of the substrate so as to help avoid insertion of the substrate in the dispenser in an inside out manner.

When the on/off switch is moved to the on position, the finger moves away from covering an exit of the shell (permit-ting the use-up cue chemical to continue to diffuse). When operation of the device is suspended by movement of the on/off switch, the finger again covers the exit of the shell, preserving the use-up cue chemical when the fan is off, and better coordinating the use-up cue life to that of the impregnated substrate portion.

Biasing of the finger by a spring portion of the switch can cause the finger to rest in a "third" rotational position when the substrate is not present in the device. This position is preferably pointing more than 45 degrees outward/upward. When the finger is so positioned a cam edge of the cam projection can only move the finger rotationally away from an operational position (e.g. clockwise). Thus, absent the substrate, the blower won't work even if a consumer tries to move the on/off switch towards an on position. This is a signal to the consumer that they should first install the substrate before use of the blower.

When the substrate is positioned properly in the device, it will rotationally drive the edge of the finger downward to the second "ready" rotational position. This is a position from where the cam edge can then drive the finger downward to an operational position. Hence, positioning the substrate in the device enables, but does not by itself activate, blower operation.

When the finger is in the second rotational position the cam projection on the shutter extends through a through slot on the substrate to be ready to drive the finger to the first rotational position with a further movement of the on/off tab. In this position enough return force is placed on the spring switch so as to activate its internal connection and enable blower operation.

The devices and refills of the present invention have a variety of important advantages. A consumer merely needs to operate a single on/off switch to control blower operation, shut off the entry and exit of air from the external environment between uses, and close off use-up cue chemical diffusion between uses. Structures associated therewith prevent motor operation when the impregnated refill has not yet been installed, and also prevent improper installation of the substrate.

These devices and refills are relatively inexpensive to produce, and are suitable for consumers to understand and use without extensive instructions. Further, these devices can be made lightweight, and thus can be worn hanging from a clothing item.

The foregoing and other advantages of the present invention will be apparent from the following description. In the description that follows, reference is made to the accompanying drawings which form a part thereof, and in which there is shown by way of illustration, and not limitation, a preferred embodiment of the invention. As this embodiment is merely illustrative, it is not intended to represent the full scope of the invention. Thus, reference should therefore be made to the claims herein for interpreting the scope of the invention.

BRIEF DESCRIPTION OF THE DRAWINGS

FIG. 1B is a view similar to FIG. 1A, but with a shutter of the dispenser shown in the open position and the device on;

DETAILED DESCRIPTION OF THE INVENTION

Figure 1A:
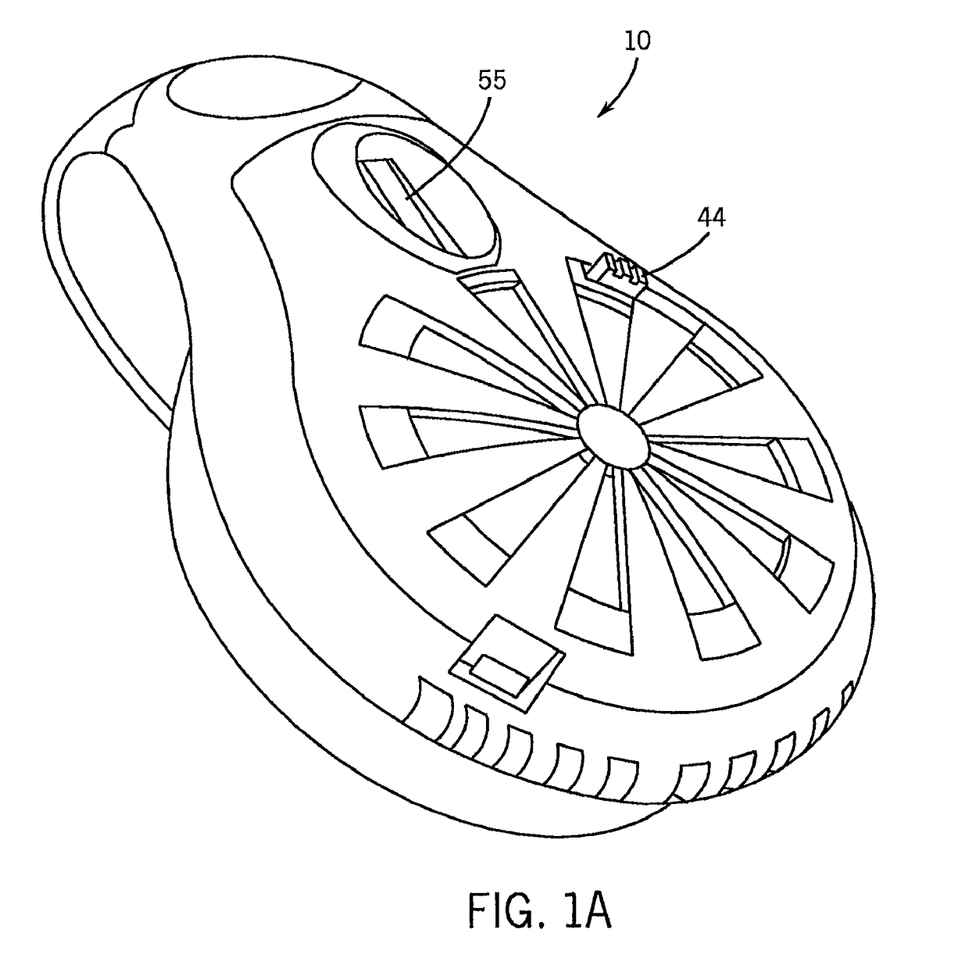
FIG. 1A is a left lower frontal perspective view of a preferred dispenser device of the present invention, in an "off" position.
Figure 1B:
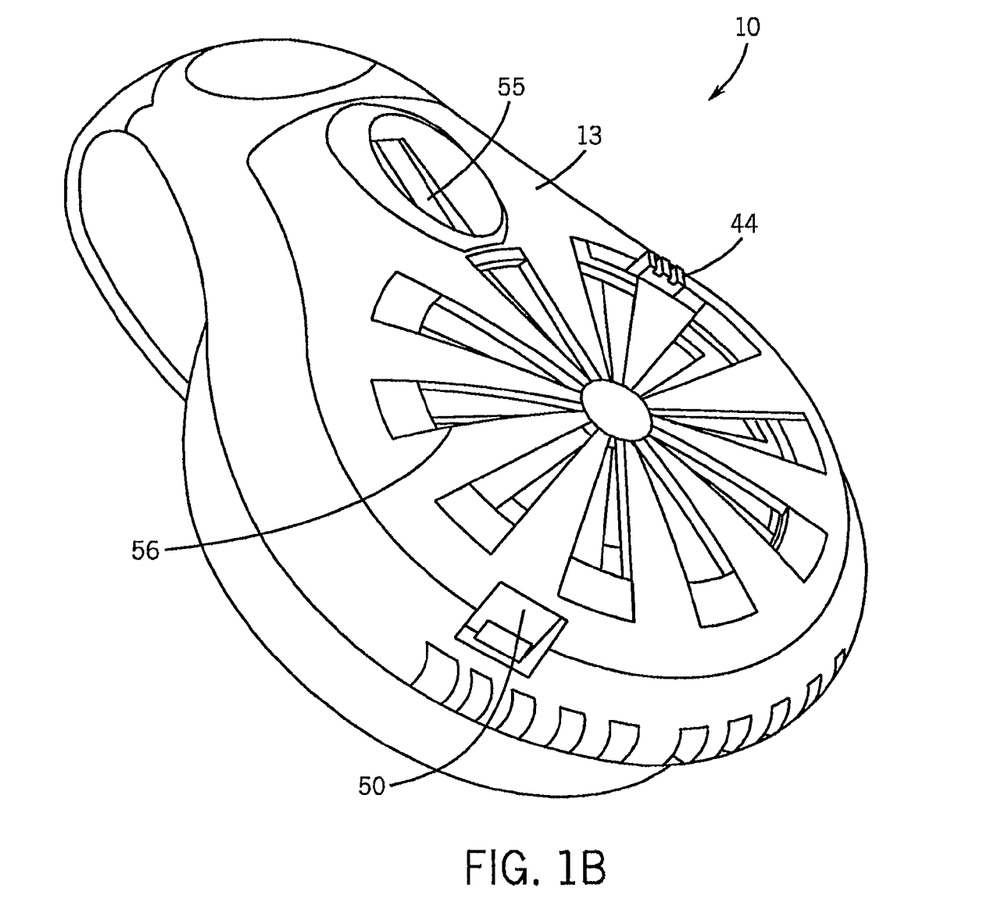
Figure 2:
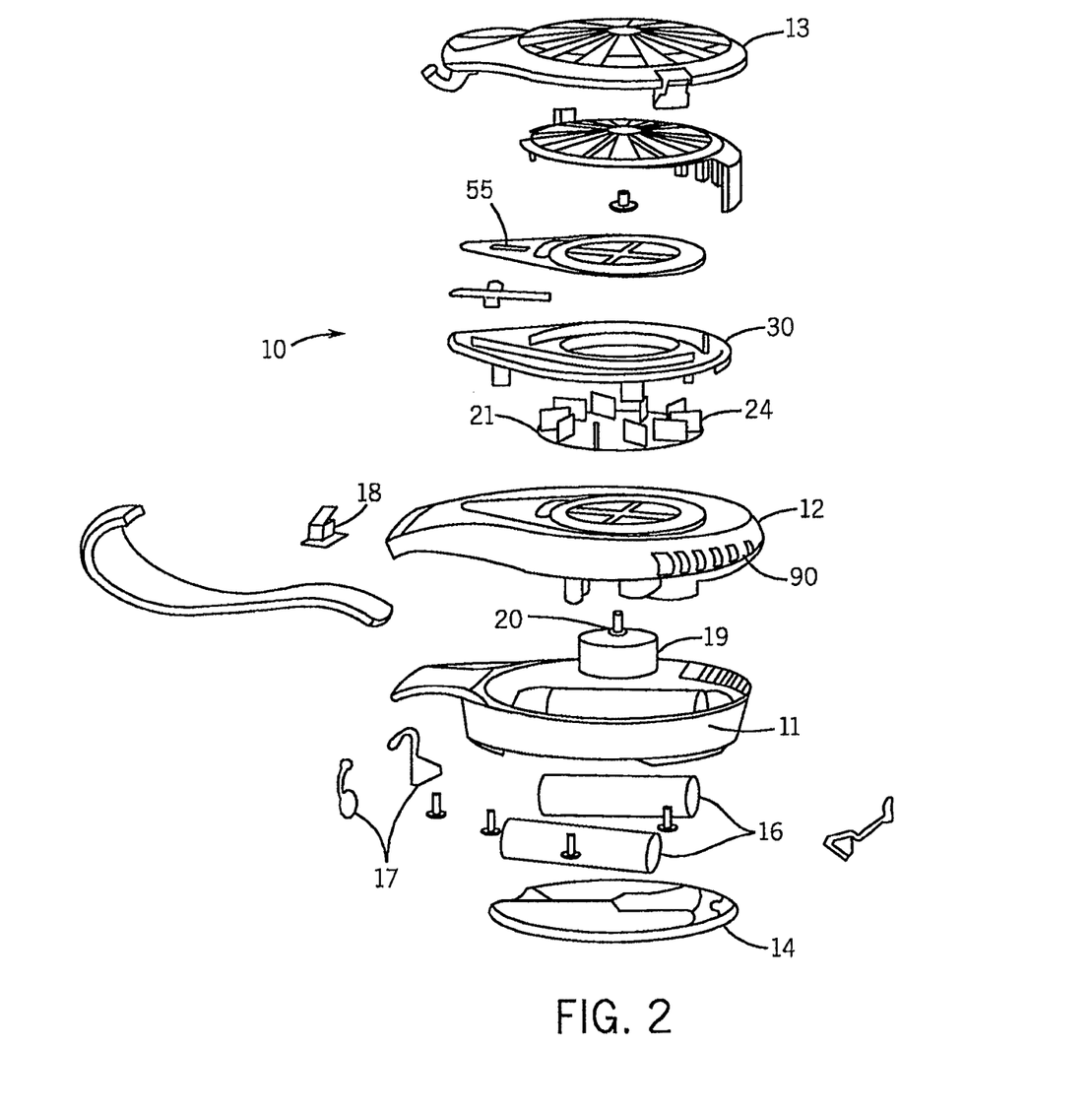
FIG. 2 is an exploded perspective view of the device of FIG. 1.

Referring first to FIGS. 1A, 1B and 2, there is shown a dispensing device 10. It has a main housing section 11, an intermediate housing section 12, an outer cover section 13 and a base cover section 14. The region between the main housing section 11 and the base cover section 14 houses the primary electrical parts.

In this regard, there are two AA batteries 16 which are in electrical contact with linkages 17, that in turn are connected to a spring-type switch 18, which (when the switch is closed) powers a small motor 19. An example of this type of switch is a micro-leaf switch of the sort available from the Wealth Metal Factory Ltd. of Hong Kong, China.

The motor 19 has a stem 20. That stem can be linked to the center of rotor 21 having vanes 24. When the motor receives power, stem 20 rotates and carries with it the rotor 21. The vanes on the rotor are aligned such that the rotation sucks air in through the openings 56 of the outer cover section 13 and then forces the air radially outward.

Figure 3:
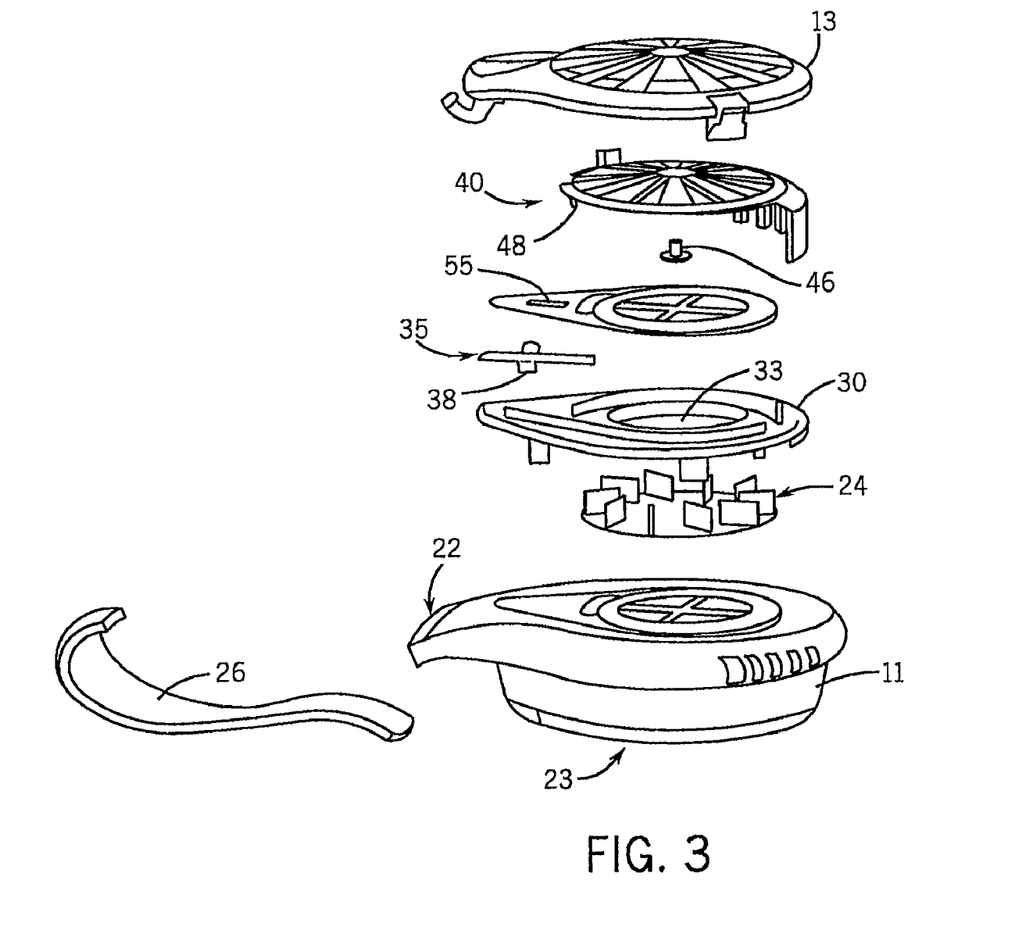
FIG. 3 is a view similar to FIG. 2, but with several of the parts assembled into a sub-unit.

As will be apparent from viewing FIG. 3, there can be formed a subassembly 23 of parts 11, 12, 14 and 16-20. This subassembly is created through the use of screws and snap fit connections.

A clip 26 can be mounted to the subassembly 23. Then, table 30 can be mounted so as to position the rotor behind it, yet permitting air to pass through its central hole 33.

The table mounts a finger 35 on its outer surface. Initially, spring-type switch 18 is positioned to bias the finger clockwise along the finger's longitudinal axis with side extension 38 pointed somewhat outward. See FIG. 7A for a showing of this "third" position.

Figure 4:
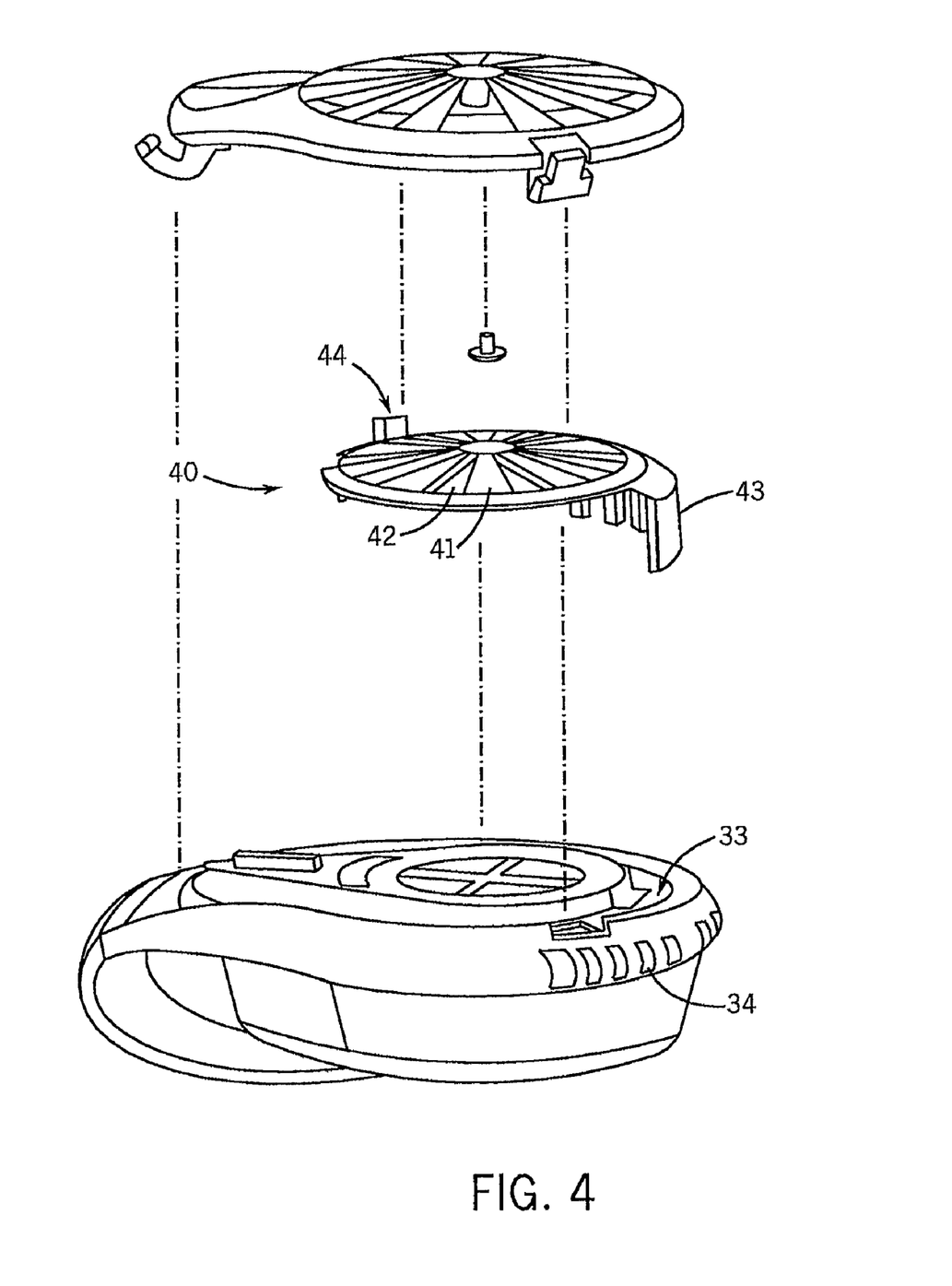
FIG. 4 is a view similar to FIG. 3, but with even more of the parts assembled together.

Shutter 40 is best understood from FIG. 4. It is bolted to the outer cover section 13 with bolt 46 so as to be able to rotate relative thereto. The shutter has triangular closures 41, triangular openings 42, control feet 43 and a control tab 44. It also has a cam projection 48 which is generally triangular in side view.

Figure 5:
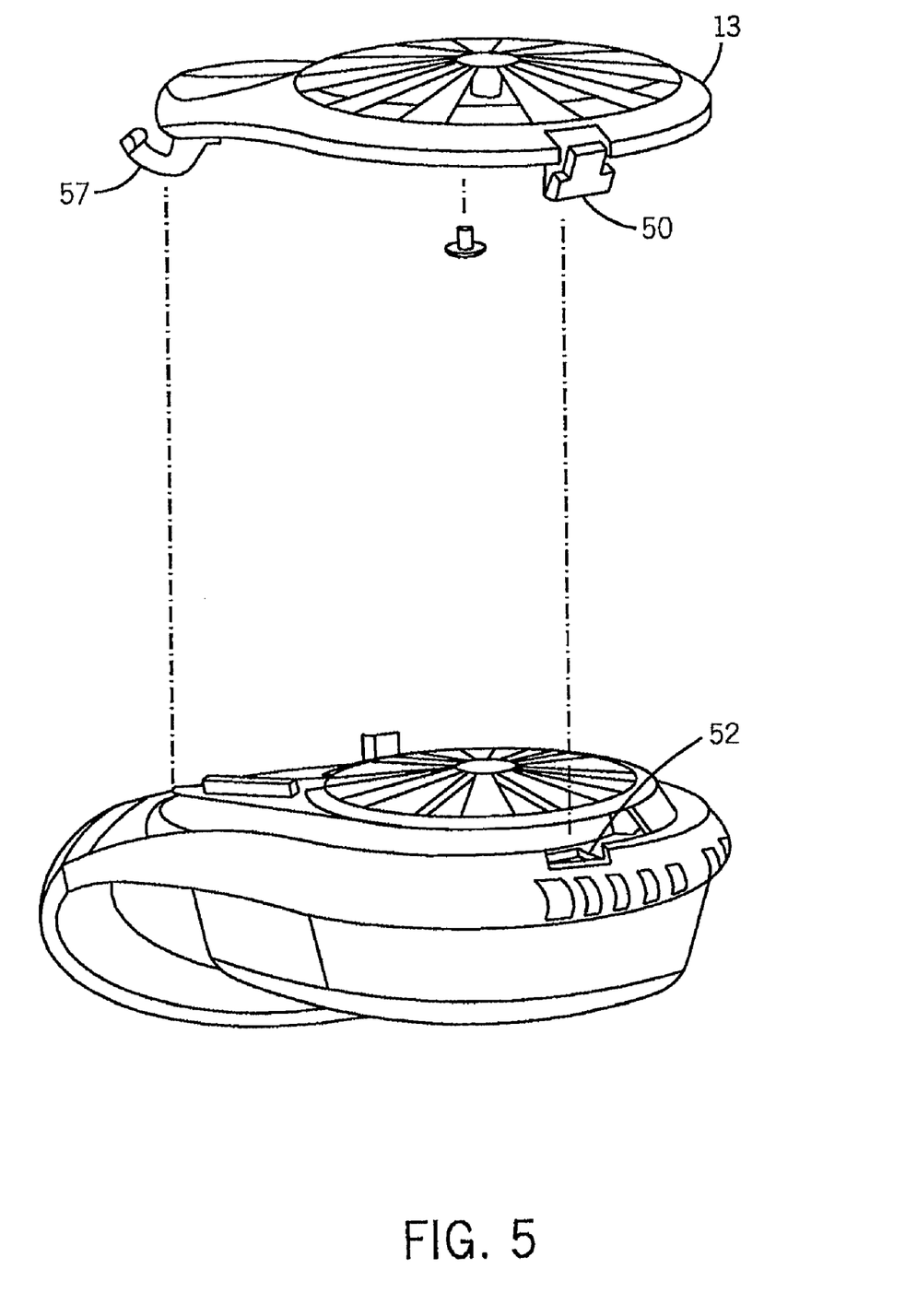
FIG. 5 is a view similar to FIG. 4, but with still more of the parts assembled together.
Figure 6:
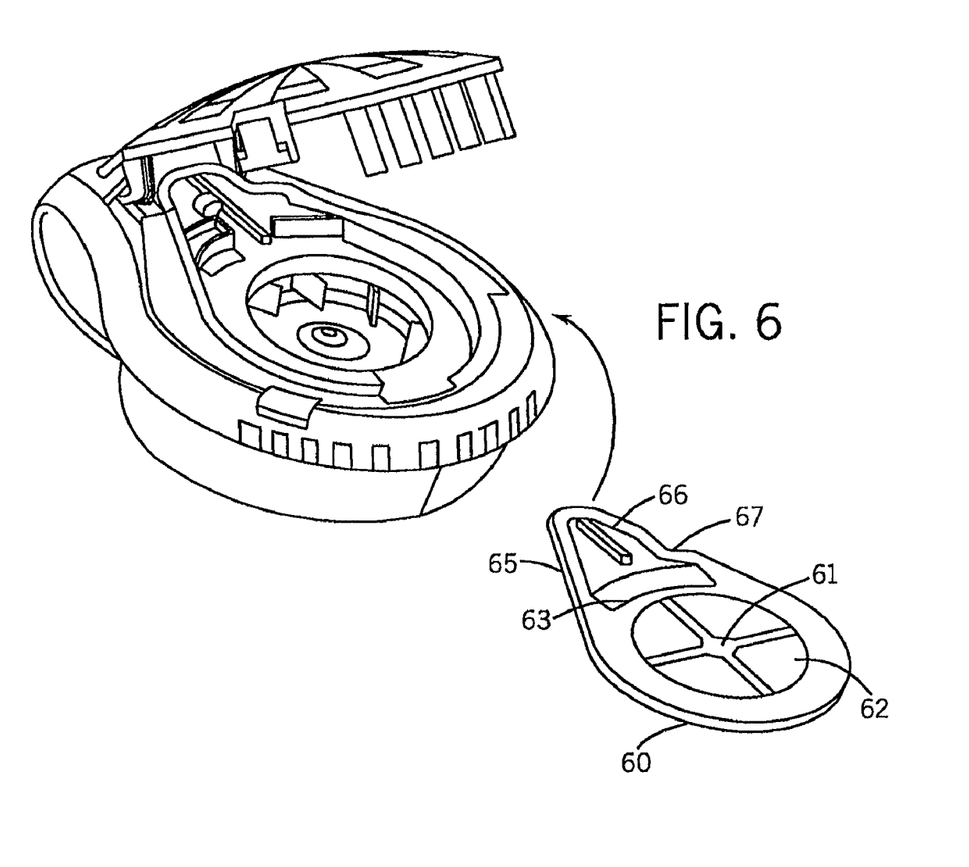
FIG. 6 is another perspective view of the FIG. 1A device, but with the front cover opened, and refill substrate not yet installed.

The outer cover section 13 has an oval viewing opening 55 and triangular air openings 56. Note also the cover hinge 51 which permits the cover to pivot as shown in FIG. 6, and the locking tab 50 which interacts with element 52 (shown in FIG. 5) to keep the outer cover section closed when that is desired.

Refill unit 60 is generally slab-like. In plan view it has an essentially tear-drop shaped overall appearance, with a generally circular portion at one end and a generally triangular portion at another end. There is a spoke support 61 across a circular opening through the slab. There is also an arc-shaped slot 63, and a use-up cue shell 66.

Across the spoke support 61 is positioned a fabric 62. When air is sucked by the rotor 21, air will be sucked through the fabric 62. The choice of the fabric, and its porosity, the speed of the air flow, and the vapor pressure of the active, are the main factors in coordinating the speed of use up of the active with the speed of use up of the use-up cue.

By impregnating the fabric 62 with an appropriate air treatment chemical, air entering the device will pick up some of the volatile chemical, and dispense it out of the device. Particularly preferred actives are those described in U.S. Pat. No. 6,582,714 or other synthetic pyrethroids. For use in controlling mosquitoes it is preferred to use metofluthrin from Sumitomo Chemical (trade name SumiOne). The impregnation material can be pure active, or for ease of handling the material can be dissolved in a hydrocarbon or other solvent. Alternatively, or in addition, the fabric may also bear a fragrance, a deodorizer, or other air treatment chemical.

For mosquito control it is preferred to use an airflow rate through the device at about 4 to 6 cubic feet per minute (0.113 to 0.170 cubic meters per minute). It is also preferred to have the fabric configured so that the pressure drop across the substrate is no more than 40 Pa. Suitable substrates can be made of woven or non-woven materials providing only minimal resistance to the airflow.

The substrate should also be capable of holding active ingredient dosed onto the material and also allow ready migration of the active to the surface of the substrate so as to allow its evaporation in response to the airflow. For an active ingredient that is hydrophobic and migrateable at common environmental temperatures between about 10° C. and 40° C. (e.g. metofluthrin), suitable materials include, only by way of example, polyester, polypropylene, cotton, cellulose, polyrayon, and other similar fabrics. These can be non-wovens with basis weights ranging from 10 gsm to 40 gsm, fabricated from synthetic, natural, or combined synthetic and natural polymeric materials.

The ideal substrate should also allow for wicking of the active ingredient following dosing so as to ensure efficient distribution throughout the substrate, and thereafter allow migration of active ingredient to the substrate's surface to replenish the active ingredient that is being evaporated by the passing airflow. Dosing may be by dropping, spraying, printing, or other conventional delivery of a liquid active ingredient to the substrate. A particularly desirable fabric is a non-woven felted material with a basis weight of 20-30 gsm fabricated from polyethylene terephthalate.

Note that one side of the essentially triangular portion is straight (at 65) and the other is indented (at 67). This slight lack of symmetry is designed to accommodate a corresponding slight lack of symmetry along the top/outer side of table 30, and to thereby prevent a consumer from installing the refill unit 60 inside-out.

Figure 7A:
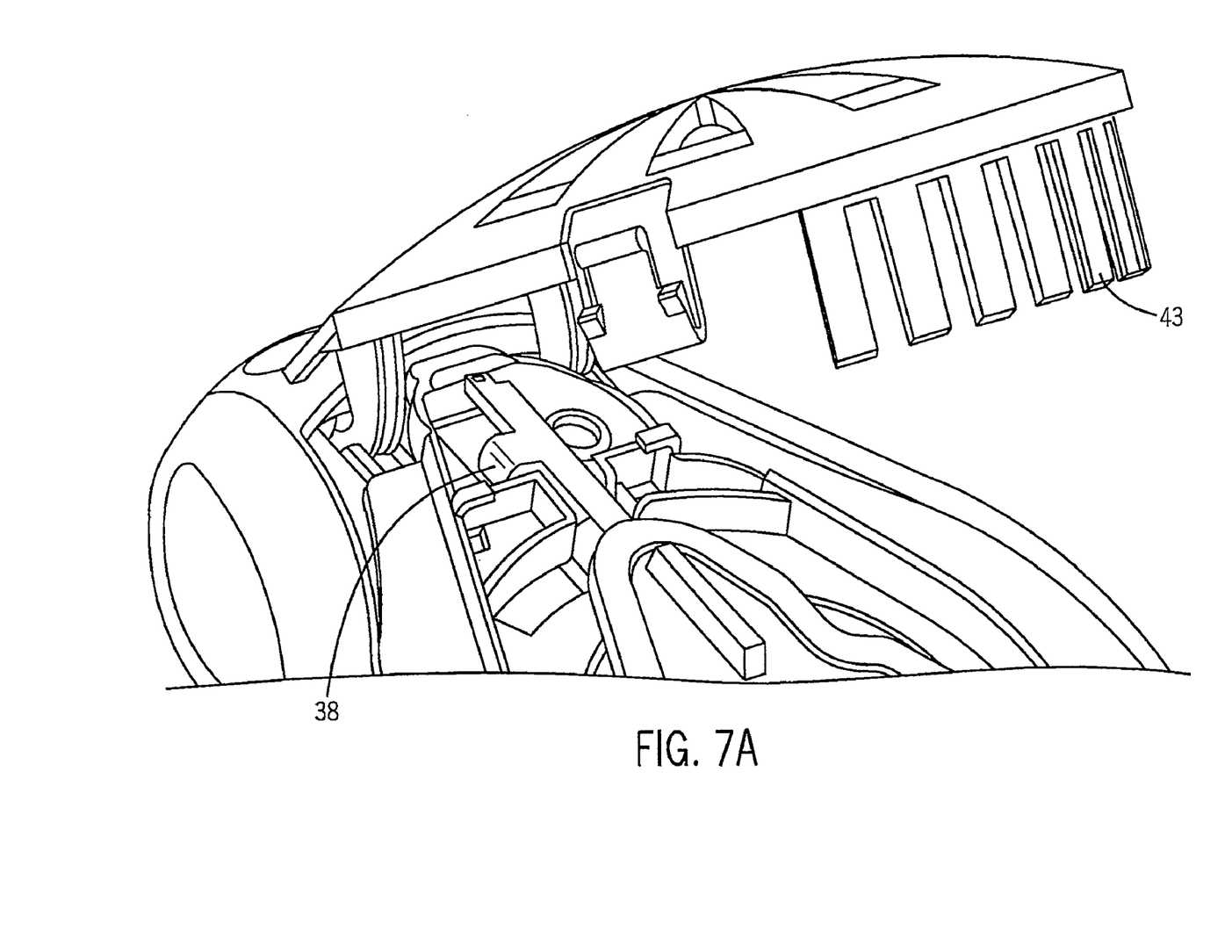
FIGS. 7A-7C are enlarged views showing how the device progressively appears when starting from the FIG. 6 position, as the refill is moved into the device.

As shown in FIG. 7A (see also FIG. 8A) when the refill unit is not yet in the device, finger 35 is biased by the spring-type switch 18 (FIG. 2) to a position such that extension 38 is pointed significantly upwardly/outwardly. When this is the case, attempted movement of the projection 48 (as the shutter is rotated) would not cause the extension 38 to rotate counterclockwise to the FIG. 7B position. Rather it moves only slightly clockwise until hitting an internal stop. Because counterclockwise rotation is needed to cause the spring-type switch 18 to complete the circuit to the motor, absent the presence of the refill the fan won't operate. This sends an immediate message to a consumer that they need to do something else to make the system work (e.g. install a refill unit).

Figure 7B:
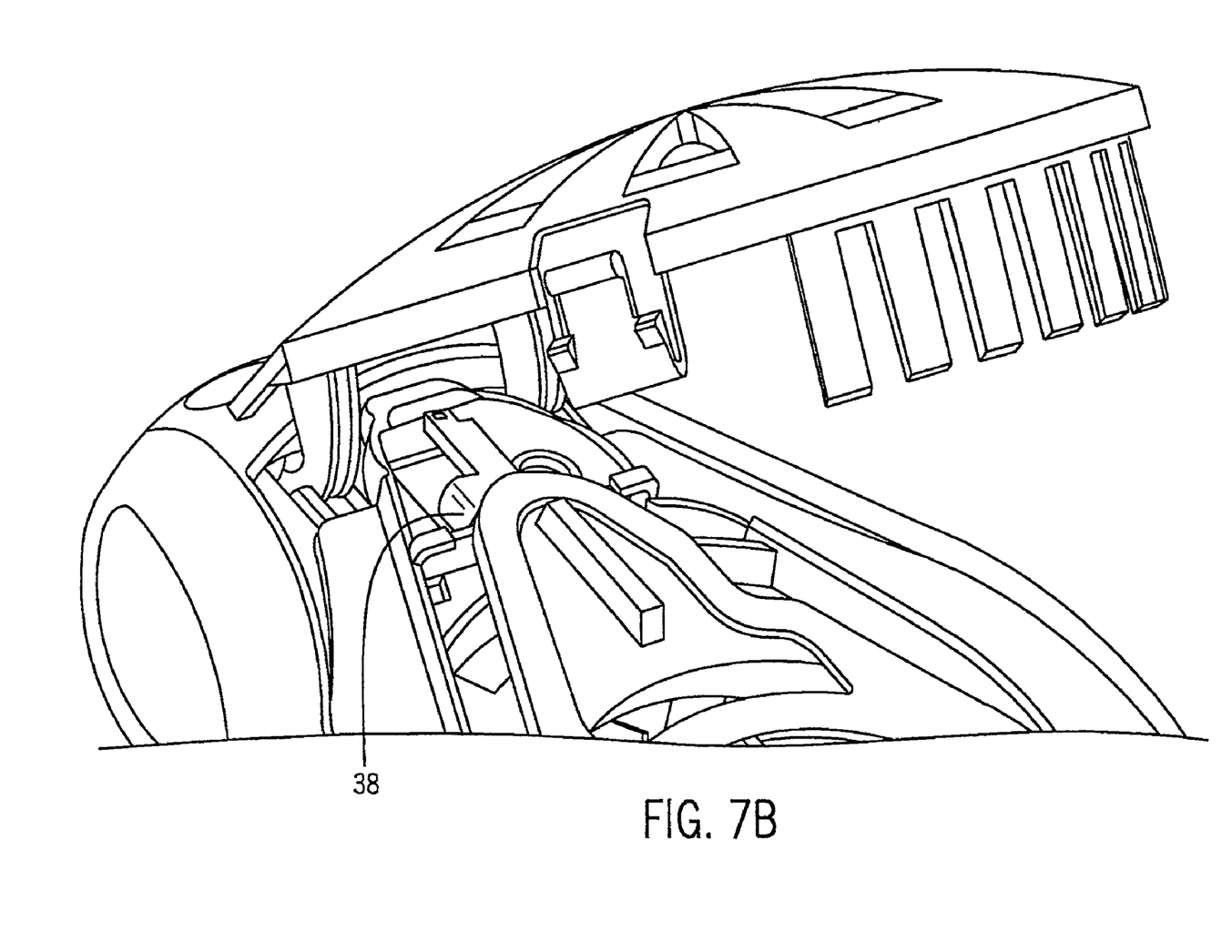
Figure 7C:
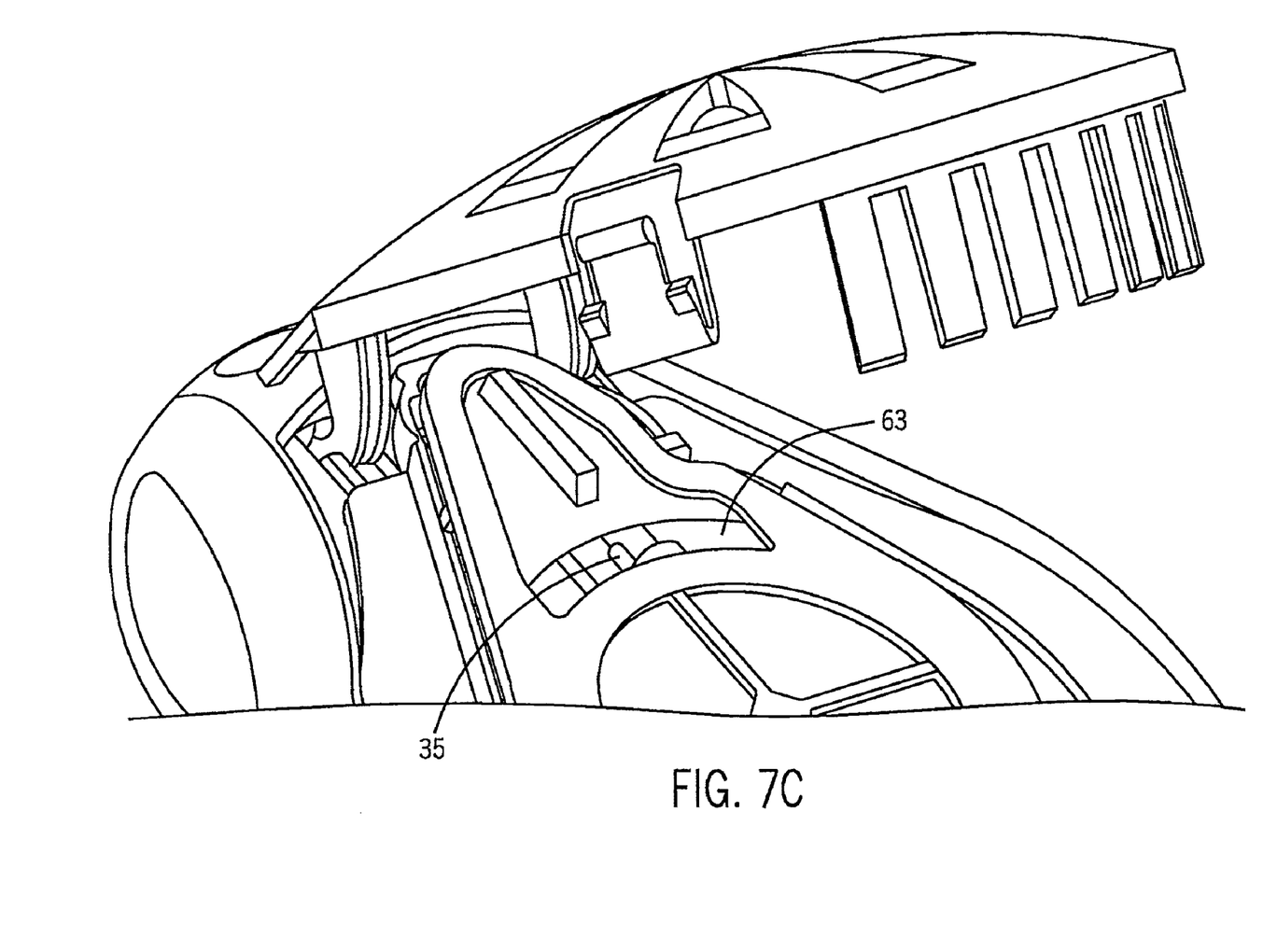
Figure 8A:
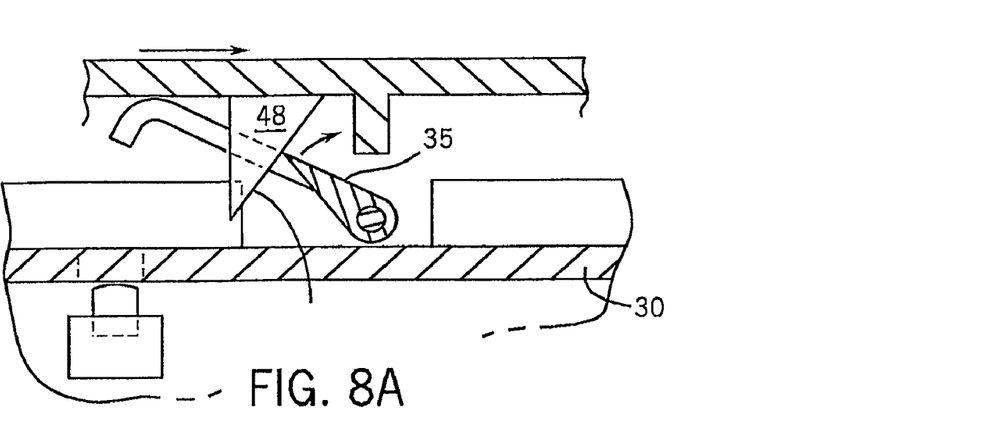
FIG. 8A shows how the cam will drive the finger clockwise absent a refill being present.
Figure 8B:
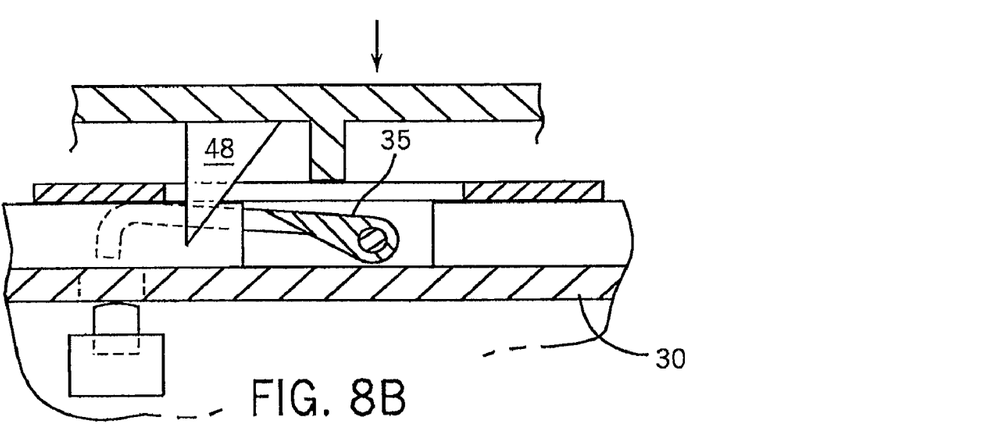
FIG. 8B shows how the presence of a refill can set up the finger to be ready for future counterclockwise movement.
Figure 8C:
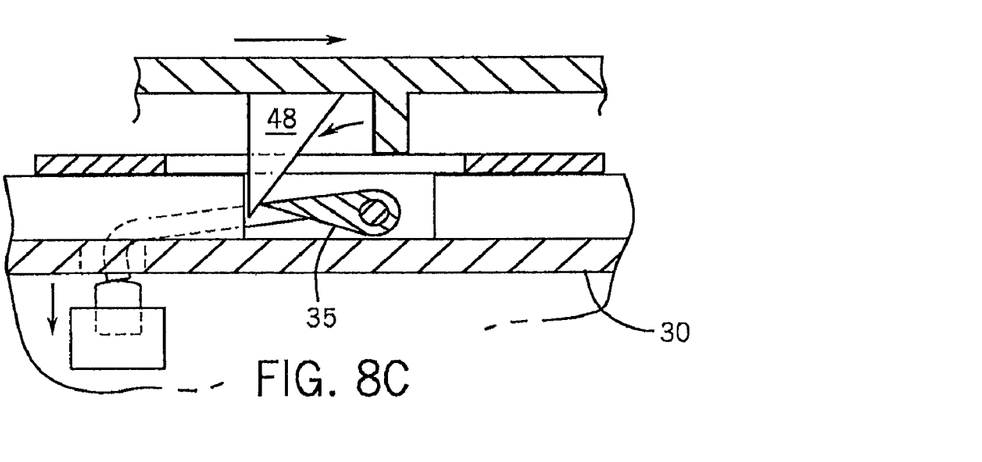
FIG. 8C shows how further movement of the on/off tab once the device has reached the FIG. 8B position will cause the finger to move further counterclockwise to activate the electronics.

As the refill is moved into place, as shown in FIG. 7B (see also FIG. 8B), it first causes the extension 38 to rotate along the finger's longitudinal axis from the third to the second position. However, the extent of the rotation at that point is still not enough to cause the fan to turn on. Rather, that occurs only when the projection 48 is projecting through the arc-shaped slot 63. Then, as the shutter is rotated, the projection 48 is driven along the arc-shaped slot 63 to permit its inward cam end to contact a part of the finger 35. As seen in FIG. 8C, the cam surface of the projection then drives the finger to complete its rotation to the "first" position. When this happens there is sufficient resisting force so as to cause the spring-type switch 18 to complete its circuit. Hence, the refill is necessary for any fan operation, but not sufficient by itself.

Note the multiple functions of the shutter 40. When one moves the control tab 44 from the FIG. 1A position to the FIG. 1B position, the triangular closures 41 move from a position where they cover openings 56 to a position where they let air pass there through as shown in FIG. 1B. At the same time there is a rotation of feet 43 from a position where the outlet openings 90 in intermediate housing section 12 are covered to one where they are uncovered. Thus, the shutter can completely close off the impregnated fabric 62, as well as the use-up cue area, between uses, thereby prolonging their life when the fan is off. The same shutter system also controls fan operation.

As described in the co-pending application U.S. Ser. No. 11/609,923, filed Dec. 13, 2006, referred to above, a variety of chemicals can be used to provide a visual indicia of the extent of use by virtue of their disappearance or change. As the use-up cue chemical, it is preferred to use a volatile liquid material that diffuses out of a shell, as described in that application. There is dye in the liquid so it can be easily seen when present. For example, one could use a dye like Fat Blue B 01 available from Clariant.

The shell 64 can be made of transparent polyethylene terephthalate. For the use-up cue chemical it is most preferred to place a volatile solvent such as Norpar 12, a hydrocarbon from ExxonMobil Chemical Company in the use-up cue shell 64, or to use that with a dye. Then, it is covered with a permeable layer such as an ultra low density polyethylene film (ULDPE) or a low density polyethylene film (LDPE). That is in turn covered before use by an impermeable peel-off layer, such as a peel-off layer or film having aluminum foil layer, preferably reinforced by an outer polyester layer. Immediately prior to use one can then peel off the peel-off layer, exposing the permeable layer at the back side of the shell.

When the finger 35 is not covering the permeable layer, the volatile can slowly seep out of the shell, providing a visual cue as to the extent of use up. This chemical is then blown out of the device by the fan, or otherwise seeps out of the device. As the consumer sees less color in the transparent window of the shell 64 they will know the use status (because absence of color means the device is used up).

When the device is off, as shown in FIG. 7A, the extension 38 will essentially cover the back side of the use-up cue. Hence, the shutter operates to avoid premature use up signals.

In operation the device will be clipped on a belt, purse or the like using clip 26 for that purpose. Air is sucked by the device in through openings 56. As the air passes through fabric 62, the active mixes into the air and the treated air is then blown radially out outlet openings 90 (preferably down along pants or dresses).

While the present device is primarily intended to be used as a wearable item carried with a human as they watch a game outdoors, or hike, or the like, it can also be laid flat, with the clip downward and front entry upward, on a picnic table or the like. When used in this manner it can provide protection to an area during a picnic or similar outdoor activity.

While the preferred embodiment has been described above, it should be appreciated that there are numerous other embodiments of the invention within the spirit and scope of this disclosure. For example, the device can be powered by a different source of energy (e.g. a solar power panel), other forms of actives can be dispensed along with or in substitution for the insect control ingredients (e.g. a fragrance or deodorizing chemical to also control body odor), and even when an insect control ingredient is dispensed it need not be one focused on controlling mosquitoes (e.g. chemicals for repelling other flying or crawling insects or pests can be used). Hence, the invention is not to be limited to just the specific embodiments shown or described.

INDUSTRIAL APPLICABILITY

Provided herein are wearable dispensing devices capable of dispensing insect control chemicals and/or other air treatment chemicals adjacent a human body, and refills for use therewith.

What is claimed is:

1. A refill substrate suitable for use as part of a dispensing device, the dispensing device being of a type comprising:
   a housing with an inlet and an outlet and an electrically powered fan to pull air in through the inlet and exhaust the air through the outlet, creating an air stream through the housing;
   a switch for turning the fan on and off;
   a movable shutter that blocks the air flow when in a first, closed position and allows the air to flow when in a second, open position, the shutter having a projection thereon that interacts with the switch so that moving the shutter to the second, open position activates the switch to turn on the fan;
   a rotatable finger that must be rotated by interaction with the projection of the shutter before the switch can be activated;
   a table to receive and hold a substrate exposed to the air stream, wherein the substrate bears an air treatment chemical to be dispensed, with the substrate held in interactive relation with the finger so as to partially rotate the finger from a designated position when no substrate is held by the table, to a selected position when a substrate is held by the table, and wherein when the finger is in the selected position it can be further rotated there from by movement of the projection as the shutter is moved to activate the fan;
   the refill substrate comprising:
   an air-permeable structure containing the air treatment chemical to be dispensed; and
   a surface positioned to interact with the finger so as to rotate it to the selected position.

2. The refill substrate of claim 1, further comprising a use-up cue such that, when the substrate is in place on the table of the dispensing device, the use-up cue changes appearance by evaporation of a material in a direction toward the table and at a location such that a side extension of the finger, when the shutter is in its closed position, blocks evaporation of material from the use-up cue.

3. A refill substrate for use with a wearable air treatment chemical dispenser, the refill substrate comprising:
   a slab structure having opposed facing surfaces;
   a through hole extending between the facing surfaces;

an air permeable sheet extending across the through hole, the sheet bearing a volatile insect repellent; and a support beam extending at least part way across the through hole to support the sheet;

wherein the slab structure also has a shell cavity retaining a use-up cue chemical, the cavity having an essentially transparent wall along one of the opposed facing surfaces;

wherein there is a through slot extending through the thickness of the slab structure and positioned between the air permeable sheet and the shell cavity.

4. The refill substrate of claim 3, wherein the shell cavity is covered by a peel-off cover along the other of the opposed facing surfaces.

5. The refill substrate of claim 3, wherein there is an indentation along a peripheral portion of the substrate so as to help avoid insertion of the substrate in the dispenser in an inside out manner.

* * * * *